United States Patent
Shah et al.

(10) Patent No.: US 10,117,821 B2
(45) Date of Patent: Nov. 6, 2018

(54) TOPICAL LIGHTENING COMPOSITION AND METHODS OF USE THEREOF

(71) Applicant: Avon Products, Inc., Suffern, NY (US)

(72) Inventors: Arvind N. Shah, Suffern, NY (US); Uma Santhanam, Tenafly, NY (US); Sungham Yim, Lincoln Park, NJ (US)

(73) Assignee: Avon Products, Inc., Rye, NY (US)

( * ) Notice: Subject to any disclaimer, the term of this patent is extended or adjusted under 35 U.S.C. 154(b) by 756 days.

(21) Appl. No.: 14/379,520

(22) PCT Filed: Feb. 26, 2014

(86) PCT No.: PCT/US2014/018692
§ 371 (c)(1),
(2) Date: Aug. 19, 2014

(87) PCT Pub. No.: WO2014/163896
PCT Pub. Date: Oct. 9, 2014

(65) Prior Publication Data
US 2016/0235646 A1  Aug. 18, 2016

Related U.S. Application Data

(60) Provisional application No. 61/777,081, filed on Mar. 12, 2013.

(51) Int. Cl.
| | |
|---|---|
| *A61K 8/00* | (2006.01) |
| *A61K 8/67* | (2006.01) |
| *A61Q 19/02* | (2006.01) |
| *A61K 8/46* | (2006.01) |
| *A61Q 19/08* | (2006.01) |
| *A61K 8/06* | (2006.01) |

(52) U.S. Cl.
CPC ............... *A61K 8/675* (2013.01); *A61K 8/06* (2013.01); *A61K 8/46* (2013.01); *A61Q 19/02* (2013.01); *A61Q 19/08* (2013.01); *A61K 2800/49* (2013.01); *A61K 2800/592* (2013.01); *A61K 2800/596* (2013.01); *A61K 2800/782* (2013.01)

(58) Field of Classification Search
None
See application file for complete search history.

(56) References Cited

U.S. PATENT DOCUMENTS

| 6,562,321 B2 | 5/2003 | Ptchelintsev et al. |
| 2002/0141953 A1 | 10/2002 | Ptchelintsev et al. |
| 2006/0216254 A1 | 9/2006 | Majmudar et al. |
| 2010/0055059 A1 | 3/2010 | Criton et al. |
| 2012/0315344 A1 | 12/2012 | Mahalingam et al. |

FOREIGN PATENT DOCUMENTS

| EP | 2666814 A1 * | 11/2013 | ......... G03G 15/0233 |
| WO | 0249580 A1 | 6/2002 | |
| WO | 2012020070 A2 | 2/2012 | |

OTHER PUBLICATIONS

David Brown et al., Comparison of the pigment lightening effects of thiodipropionate acid and its ester with hydroquinone, Feb. 2007, Journal of the American Academy of Dermatology, vol. 56, Issue 2, Supplement 2, p. AB94.*
European Search Report to corresponding EP Application No. 14778546.3, dated Jun. 1, 2016.

* cited by examiner

*Primary Examiner* — Nannette Holloman
(74) *Attorney, Agent, or Firm* — Brian P. McCloskey

(57) ABSTRACT

Embodiments of the invention are generally directed to compositions comprising lightening agents, nicotinamide and 3,3'-thiodipropanoic acid, in a cosmetically acceptable vehicle, articles of manufacture, and methods of use thereof. The compositions and methods of described herein are effective to lighten an area of skin in need of lightening, such as but not limited to, a subject having overall dark complexion, pigmented skin discoloration, freckles, age spots, liver spots, sun damage, tans, pigmented acne marks, scars, pigmented birthmarks, hyperpigmentation, post-inflammatory hyperpigmentation, post-injury hyperpigmentation, melasma, cholasma, after-burn scar, nail stain, yellowing of skin, dark circles under eyes, and the like. The composition may include additional ingredients accordingly for a colored cosmetic, moisturizer, cleanser, toner, and the like.

12 Claims, No Drawings

TOPICAL LIGHTENING COMPOSITION AND METHODS OF USE THEREOF

CROSS-REFERENCE TO RELATED APPLICATIONS

This application claims priority benefit, under the national stage entry under 35 U.S.C. 371 of International Application No. PCT/US14/18692, filed on Feb. 26, 2014 the contents of which application are hereby incorporated by reference in their entirety. This patent application claims priority to U.S. Patent Application Ser. No. 61/777,081, filed on Mar. 12, 2013. The entirety of the aforementioned application is incorporated herein in its entirety by reference.

FIELD OF INVENTION

The invention relates generally to cosmetic and dermatological compositions and methods for reducing pigmentation in the skin. The compositions of the invention comprise thiodipropionic acid or a derivative thereof in combination with nicotinamide or a derivative thereof. The compositions may be applied topically to skin to reduce pigmentation in the area of application.

BACKGROUND

Several skin conditions are associated with the overproduction or unwanted production of melanin the skin, including age spots, freckles, and liver spots. The synthesis of melanin occurs in melanocyte cells in the skin and is a complex process involving several biochemical pathways. Some skin lighteners or depigmenting agents, such as hydroquinone and kojic acid, act as inhibitors of tyrosinase, an enzyme that has its catalytically active domain within organelles known as melanosomes. Tyrosinase converts phenols, including tyrosine, to ortho-quinones which are subsequently converted to melanin within the melanosomes. Other skin lighteners, such as serine-protease inhibitors, act by disrupting the transfer of the melanosomes from melanocytes to the keratinocytes where melanin is deposited.

While skin lighteners such as hydroquinone and kojic acid have found some utility in cosmetic and dermatological products, there remains a continuing need for products that effectively reduce pigmentation of skin. It is therefore an object of the invention to provide compositions and methods for reducing pigmentation in human skin, including, for example, treatment of hyperpigmentation, unwanted pigmentation, age spots, liver spots, freckles, and the like. The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF INVENTION

In accordance with the foregoing objectives and other, the invention provides compositions and methods for reducing pigmentation in human skin. The compositions and methods may treat hyperpigmentation conditions, including those associated with UV damage and chronological aging, including without limitation treating, ameliorating, diminishing the appearance of, or preventing age spots, liver spots, freckles, and the like. The compositions and methods are also useful for reducing otherwise unwanted pigmentation, including overall lightening of the skin.

In one aspect of the invention, compositions are provided for reducing pigmentation in the skin comprising an effective amount of 3,3'-thiodipropionic acid (TDPA), or esters or salts thereof, for inhibiting tyrosinase in combination with an effective amount of nicotinamide or its salts or derivatives for inhibiting melanosome transfer. The compositions may be characterized in that the effective amounts of thiodipropionic acid (TDPA), or esters or salts thereof, and nicotinamide, or salts or derivative thereof, provide a reduction in melanin that is at least 25% greater, or at least 50% greater, than achieved by the effective amount of either component alone, i.e., in the absence of the effective amount of the other component. In some embodiments, the compositions may be characterized in that the effective amounts of thiodipropionic acid (TDPA), or esters or salts thereof, and nicotinamide, or salts or derivative thereof, provide at least an approximately additive reduction in melanin synthesis, meaning that the resultant reduction in melanin is approximately the sum of the reductions achieved by the individual components alone. In other embodiments compositions are provided comprising combinations of thiodipropionic acid (TDPA), and esters thereof, in combination with nicotinamide or its salts or derivatives, which provides more than an additive reduction in melanin synthesis, meaning that the resultant reduction in melanin is more than the sum of the reductions achieved by the individual components alone.

In some implementations of the invention, the effective amount of thiodipropionic acid (TDPA), or esters or salts thereof, may range from about 0.001% to about 10% by weight, typically from 0.01% to about 5% by weight, or from about 0.1% to about 2.5% by weight, or from about 0.5% to about 1.5% by weight, based on the total weight of the composition. In other implementations, the effective amount of nicotinamide or derivative thereof, may range from about 0.0001% by weight to about 5% by weight, typically from 0.001% to about 5% by weight, or from about 0.01% to about 2.5% by weight, based on the total weight of the composition. The weight ratio of the effective amount of thiodipropionic acid (TDPA), or esters or salts thereof, to the effective amount of nicotinamide, or derivative thereof, may range from about 100:1 to about 1:100, but will typically be in the range of about 50:1 to about 1:50, more typically from about 25:1 to about 1:25, or from about 15:1 to about 1:15; about 10:1 to about 1:10; about 5:1 to about 1:5; about 3:1-about 1:3; about 2:1-about 1:2; and about 1:1. In one embodiment, the weight ratio of thiodipropionic acid (TDPA), or esters or salts thereof, to the effective amount of nicotinamide, or derivative thereof, is about 10:1.

The compositions of the invention will typically include a cosmetically or dermatologically acceptable vehicle, which may be in the form of, for example, a serum, a cream, a lotion, a gel, or a stick, and may comprise an emulsion (e.g., water-in-oil, oil-in-water, water-in-silicone, silicone-in-water, polyol-in-silicone, silicone-in-polyol emulsion, etc.), or may comprise an aqueous or ethanolic vehicle, silicone (e.g., cyclomethicone, dimethicone, etc.), hydrocarbon (e.g., petrolatum, isododecane, etc.), ester oil (isopropyl myristate, myristyl myristate, or the like. The vehicle may further comprise an emulsifier, gelling agent, structuring agent, rheology modifier (e.g., a thickener), film former, or the like. The compositions of the invention may optionally include additional skin benefit agents such as emollients (dimethicone oils, ester oils, or hydrocarbon oils), humectants (e.g., polyols, including propylene glycol, glycerin, etc.), antioxidants (e.g., BHT, ascorbic acid, sodium ascorbate, ascorbyl palmitate, beta-carotene, etc.), vitamins (e.g., tocopherol, tocopheryl acetate, etc.), alpha-hydroxy acids (e.g., glycolic acid), beta-hydroxy acids (e.g., salicylic acid), retinoids (e.g., retinoic acid, all-trans-retinoic acid, retinaldehyde, retinol, and retinol esters such as acetates or palmitates), other anti-aging ingredients (e.g., collagen stimulators), as well as additional depigmenting agents.

In another embodiment of the invention, the compositions may include any of the following ingredients, alone or in combination: nilopala; patanga; chandana; ushira; manjshta; kumkuma; laksa; padmakesara; padmaka; yashtimadhu; ajakshira; ksheera; nyagrodhapada; and/or lodhra.

In another embodiment of the invention, the compositions may include any of the following ingredients, alone or in combination: vinyl dimethicone/methyl silsesquioxane crosspolymers; silicone crosspolymers such as caprylyl methicone (and) PEG-12 dimethicone/PPG-20 crosspolymer; MQ/T propyl resins.

It is a further object of the present disclosure to provide methods comprising topically applying such depigmenting compositions to skin. The composition may be applied once or twice daily, or more frequently, and the treatment regimen may last for as long as required to obtain the desired visible reduction in pigmentation, which may be, for example, one week, four weeks, eight weeks or longer. The compositions may be applied to human keratinous surfaces, such as skin, to treat, ameliorate, diminish, or prevent, or delay the onset of one or more of dark complexion, pigmented skin discoloration, pigmented birthmarks, hyperpigmentation, post-inflammatory hyperpigmentation, post-injury hyperpigmentation, freckles, age spots, liver spots, sun damage, tans, pigmented acne marks, scars, melasma, cholasma, after-burn scars, nail stains, yellowing of skin, or dark circles under eye.

These and other aspects of the present invention will become apparent to those skilled in the art after a reading of the following detailed description of the invention, including the illustrative embodiments and examples.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

The present invention is premised on the discovery that the combination of 3,3'-thiodipropanoic acid (TDPA) and nicotinamide (3-pyridinecarboxamide) reduces melanin in the skin to a surprising degree. This result is unexpected because TDPA provides less than additive results when combined with other tyrosinase inhibitors or melanosome-transfer inhibitors. As demonstrated in Example 1, the combination of 3,3'-thiodipropanoic acid and nicotinamide provide a far greater reduction in melanin than either of the agents alone, and achieves at least an additive reduction in melanin. Example 2 demonstrates that TDPA in combination a known tyrosinase inhibitor, Kojic acid, provides substantially less than an additive effect and, in fact, the combination is no better than Kojic acid alone. Similarly, Example 3 demonstrates that the combination of TDPA with a melanosome-transfer inhibitor likewise provides substantially less than an additive benefit. Therefore, it was not predicted that 3,3'-thiodipropanoic acid (TDPA) and nicotinamide could produce an additive reduction in melanin. The ability of an agent or combination of agents to reduce melanin in the skin may be determined by the protocol set forth in Examples 1-3.

The invention provides compositions for reducing pigmentation and/or lightening areas of the integumentary system, including but not limited to, skin, hair, lips, and nails. The compositions are, in one embodiment, topical compositions that once applied to the biological substrate result in a lightening of the biological substrate. As used herein, "skin" refers to the biological substrate of the integumentary system that includes skin, hair, lips, nails, and the like.

In some embodiments, the composition and methods are for the treatment of hyperpigmentation, which includes eradicating, reducing, ameliorating, or reversing a degree of subject pigmentation that results from increased presence of one or more of the different types of melanin biosynthesized in skin and/or follicles and deposited in hair or skin, relative to a subject's baseline pigmentation.

In some embodiments, the composition and methods are for lightening skin, which includes eradicating, reducing, ameliorating, and/or reversing a baseline degree of subject pigmentation. Lightening skin may be measured by observing changes in Fitzpatrick scale value of a subject. The Fitzpatrick Scale (aka, Fitzpatrick skin typing test or Fitzpatrick phototyping scale) is a numerical classification schema for the color of skin, and remains a recognized tool for dermatologic research into the color of skin. The Fitzpatrick Scale measures several components, including Genetic Disposition, Reaction to Sun Exposure and Tanning Habits., and classifies skin into six types: Type I (scores 0-7) refers to white, very fair skin, freckles, typical albino skin, that always burns, never tans; Type II (scores 8-16) refers to white, fair skin, that usually burns, or tans with difficulty; Type III (scores 17-24) refers to beige, which is very common, and which sometimes suffers mild burn, gradually tans to a light brown; Type IV (scores 25-30) refers to beige skin with a brown tint, which is typical of Mediterranean Caucasian skin, and which rarely burns, tans with ease to a moderate brown; Type V (scores over 30) refers to dark brown skin which very rarely burns, tans very easily; Type VI refers to Black skin that Never burns, tans very easily, and is deeply pigmented. In some embodiments of the invention, the treatments are capable of changing the treated area of skin by at least one or at least two skin type on the Fitzpatrick scale. It is to be understood that, as used herein, the terms treating and treatment include and encompass reducing, ameliorating, improving, alleviating, and/or eliminating the dermatological effects of aging and/or environmental stress, or otherwise reducing the appearance of pigmentation in the skin. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In one embodiment, the compositions are applied to the face, chest, and/or hands.

Specific benefits which may be achieved include, but are not limited to, reducing pigmentation of dark or hyperpigmented skin; reducing age spots or liver spots; reducing pigmented birthmarks, sun damage, tans, pigmented acne marks, scars; evening out or optimizing skin discoloration; decreasing the appearance of dark circles under the eyes;

treating melasma, cholasma, freckles, after-burn scars, yellowing of skin, and post-injury hyperpigmentation; lightening hair on the scalp, legs, face, and other areas where whitening and color reduction are desired; and removing or reducing nail stains.

The present composition and methods of use thereof are not limited by any particular characterization of the physiological and/or chemical effects of lightening agents. Various skin lightening pathways are known and include, for example, those that occur by decreasing melanogenesis by decreasing tyrosinase activity in melanocytes as well as inhibiting melanosome maturation. However, the lightening agents used in the present compositions and methods are believed to lighten by multiple modes of action and by inhibiting the transfer of melanin from the melanocytes to the keratinocytes.

The first component of the inventive composition is a tyrosinase inhibitor comprising 3,3'-thiodipropionic acid, a salt thereof, or an ester of 3,3'-thiodipropionic acid having the structure of formula I:

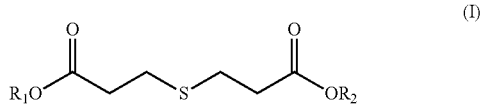

(I)

wherein $R_1$ and $R_2$ are independently selected from hydrogen, a group L, or a group $R^a$, where $R^a$ is independently at each occurrence an aliphatic $C_{1-20}$ hydrocarbon radical; an aromatic $C_{6-12}$ hydrocarbon radical; a $C_{6-20}$ alkyl-aryl hydrocarbon radical; a $C_{6-20}$ aryl-alkyl hydrocarbon radical; or a heteroaromatic radical, each of the foregoing being optionally substituted with a group R or with 1-6 heteroatoms selected from nitrogen, oxygen, sulfur, or halogen;

wherein L is a group of the form —$X_1$—$(CR^*_2)_n$—$X_2$—$(CR^*_2)_m$—$X_3$—; wherein $X_1$, $X_2$, and $X_3$ are independently at each occurrence a bond, —O—, —$NR^N$—, —S—, —$(OCH_2CH_2)_p$—, —$(CH_2CH_2O)_q$—, or a group R*, wherein "p" and "q" are independently an integer from 1 to 10, and "n" and "m" are independently an integer from 0 to 10;

R is independently at each occurrence selected from hydrogen, —F; —Cl; —Br; —I; —OH, —OR*; —$NH_2$; —NHR*; —$N(R^*)_2$; —$N(R^*)_3$; —$N(R^*)$—OH; —$N(\rightarrow O)(R^*)_2$; —O—$N(R^*)_2$; —$N(R^*)$—O—R*; —$N(R^*)$—$N(R^*)_2$; —C=N—R*; —N=$C(R^*)_2$; —C=N—$N(R^*)_2$; —$C(=NR^*)$—$N(R^*)_2$; —SH; —SR*; —CN; —NC; —(C=O)—R*; —CHO; —$CO_2H$; —$CO_2^-$; —$CO_2R^*$; —(C=O)—S—R*; —O—(C=O)—H; —O—(C=O)—R*; —S—(C=O)—R*; —(C=O)—$NH_2$; —(C=O)—$N(R^*)_2$; —(C=O)—$NHNH_2$; —O—(C=O)—$NHNH_2$; —(C=S)—$NH_2$; —(C=S)—$N(R^*)_2$; —$N(R^*)$—CHO; —$N(R^*)$—(C=O)—R*; —(C=NR)—O—R*; —O—(C=NR*)—R*, —SCN; —NCS; —NSO; —SSR*; —$N(R^*)$—C(=O)—$N(R^*)_2$; —$N(R^*)$—C(=S)—$N(R^*)_2$; —$SO_2$—R*; —O—$S(=O)_2$—R*; —$S(=O)_2$—OR*; —$N(R^*)$—$SO_2$—R*; —$SO_2$—$N(R^*)_2$; —O—$SO_3^-$; —O—$S(=O)_2$—OR*; —O—$S(=O)$—OR*; —O—S(=O)—R*; —S(=O)—OR*; —S(=O)—R*; —NO; —$NO_2$; —$NO_3$; —O—NO; —O—$NO_2$; —$N_3$; —$N_2$—R*; —$N(C_2H_4)$; —$Si(R^*)_3$; —$CF_3$; —O—$CF_3$; —$PR^*_2$; —O—P(=O)$(OR^*)_2$; —P(=O)$(OR^*)_2$; perfluoroalkyl; an aliphatic $C_1$-$C_{12}$ hydrocarbon radical; a $C_6$-$C_{12}$ aromatic hydrocarbon radical; a $C_5$-$C_{12}$ heteroaryl radical;

$R^N$ and R* are selected independently from hydrogen or a saturated, partially saturated, or aromatic $C_1$-$C_{20}$ hydrocarbon radical, optionally substituted with a group R or with 1-6 heteroatoms selected from nitrogen, oxygen, sulfur, or halogen; with the proviso that at least one of $R_1$ and $R_2$ is a group L or R*; and salts thereof.

In one embodiment the compounds of the structure of formula I are mon-esters. In another embodiment, the compounds of the structure of formula I are di-esters. In one embodiment, $R_1$ and $R_2$ are the same. In another embodiment $R_1$ and $R_2$ are different. In one embodiment, the compounds of the structure of formula I are mono- or di-esters where R1 and/or $R_2$ are each independently selected from $C_{1-20}$ aliphatic hydrocarbon radicals. In one embodiment, the compound of the structure of formula I is a dialkyl ester of TDPA. In another embodiment, the compound of the structure of formula I is a $C_{6-16}$ dialkyl ester of TDPA. In another embodiment, the ester of TDPA is di-lauryl-3,3'-thiodipropionate.

In some embodiments, 3,3'-thiodipropionate or a mono-ester thereof may be present in ionized or salt form. Suitable salts may be formed by the reaction of 3,3'-thiodipropionate or its mono-ester with a base, such as, for example, a metal (sodium) hydroxide, ammonia, or an amine.

The compositions of the invention will also comprise nicotinamide or a derivative thereof having the structure of formula II:

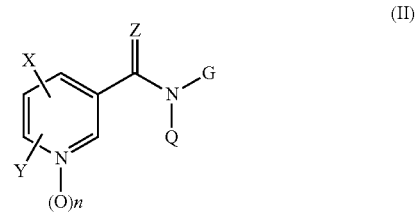

(II)

wherein "n" is an integer 0 or 1; such that when "n" is 1, the compound is an N-oxide, and where "n" is 0, the oxygen atom is not present;

Z is selected from the group consisting of O, S, NH, and $NR^N$; wherein Z is typically O;

G and Q are independently selected from the group consisting of hydrogen, $R^N$, —COR, —$CO_2R$, —C(=O)NHR, —C(=O)$NR_2$, —$PO_3R$, —$S(O)_mR$, —NHR, —N=CHR, —NR(C=O)R; and —$NRCO_2R$; where "m" is 0, 1, or 2; and wherein G and Q may together form a 3-6 membered heterocyclic ring; and where Z and G may together form a 5 or 6-member heterocylic ring; and in one embodiment, G and/or Q is a lower alkyl group (methyl, ethyl, propyl, or butyl);

X and Y are independently selected from groups R, and where X and Y may together to form 4-6 membered ring; and in some embodiments X and/or Y are hydrogen;

and where R, $R^N$ and R* are as defined above in connection with the structure of formula I; or a salt thereof.

A useful effective amount of each of the depigmenting agents, described herein, is from about 0.001% to about 10% by weight, or from about 0.005% to about 5% by weight, or from about 0.01% to about 2.5% by weight, or from about 0.05% to about 1.5% by weight, or from about 0.1 to about 1% by weight, based on the total weight of the composition. Within these ranges, useful amounts of the depigmenting agents in the compositions of the present invention may include about 0.001%, about 0.005%, about 0.01%, about 0.05%, about 0.1%, about 0.255, about 0.5%, about 1%, or about 2% by weight of the total composition. Aggregate amount of both skin lightening agents in the composition may be ascertained by adding the ranges and/or useful amounts of each depigmenting agent together from the ranges and individual numerical values given above.

In one embodiment, nicotinamide (or a salt thereof) and 3,3'-thiodipropanoic acid (or a salt thereof) are each in an effective amount to lighten skin, which amount will typically range from about 0.001% to about 5% based on the total weight of the composition. Nicotinamide or a salt thereof may be in an effective amount ranging from, for example, about 0.01% to about 0.5% (w/w), or from about 0.05% to about 0.25% (w/w), of about 0.1% based on the total weight of the composition. The effective amount of 3,3'-thiodipropanoic acid or salts thereof may be in an effective amount of, for example, about 0.1% to about 2.5% (w/w), or from about 0.5% to about 1.5% (w/w), or about 1% (w/w) based on the total weight of the composition.

The compositions can include a cosmetically or dermatologically acceptable vehicle. Such vehicles may take the form of any known in the art suitable for application to skin. The vehicle may comprise from about 50% to about 99% by weight of the composition.

The vehicle may comprise an aqueous phase, an oil phase, an alcohol, a silicone phase or mixtures thereof, and may be in the form of an emulsion. Non-limiting examples of suitable emulsions include water-in-oil emulsions, oil-in-water emulsions, silicone-in-water emulsions, water-in-silicone emulsions, polyol-in-silicone emulsions, silicone-in-polyol emulsions, polyol-in-oil emulsions, oil-in-polyol emulsions, wax-in-water emulsions, water-oil-water triple emulsions or the like. The emulsion may include an emulsifier, such as a nonionic, anionic or amphoteric surfactant, or a gelling agent.

The vehicle may comprise water; vegetable oils; mineral oils; esters such as octyl palmitate, myristyl myristate, isopropyl myristate, and isopropyl palmitate; ethers such as dicapryl ether and dimethyl isosorbide; alcohols such as ethanol and isopropanol; fatty alcohols such as cetyl alcohol, cetearyl alcohol, and stearyl alcohol; volatile silicones such as cyclomethicones, silicone oils like dimethicone, amondimethicones, and dimethiconol; hydrocarbons such as mineral oil, petrolatum, and isoparaffins such as isooctane, isododecane (IDD), isohexadecane, and isoeicosane; and (hydrogentated) polyolefins such as polyisobutene; polyols such as propylene glycol, glycerin, butylene glycol, pentylene glycol and hexylene glycol; liposomes; waxes (animal, vegetable, or synthetic); or any combinations or mixtures of the foregoing.

In one embodiment of the invention, the compositions may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors. The amounts of these various ingredients are those conventionally used in the cosmetic field to achieve their intended purpose, and range typically from about 0.01 wt % to about 20 wt % by weight of the composition. The nature of these ingredients and their amounts must be compatible with the production of the compositions of the disclosure. In another embodiment of the invention, the compositions may include any of the following ingredients, alone or in combination: nilopala; patanga; chandana; ushira; manjshta; kumkuma; laksa; padmakesara; padmaka; yashtimadhu; ajakshira; ksheera; nyagrodhapada; and/or lodhra.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans or 13-cis), and derivatives thereof, retinaldehyde, retinol (Vitamin A) and esters thereof, such as retinol palmitate, retinol acetate and retinol propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof.

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise from about 0.001% to about 10% (w/w), or from about 0.01% to about 5% (w/w) of the total weight of the composition.

The compositions may include one or more additional agents that combat pigmentation or hyperpigmentation, including tyrosinase inhibitors and/or melanosome transfer inhibitors. Special mention may be made of hydroquinone and the monobenzyl ether thereof; hydroquinone-beta-D-glucopyranoside; retinoids (e.g., retinoic acid); tretinoin; azelaic acid; Kojic acid (5-hydroxy-4-pyran-4-one-2-methyl); Mequinol (4-hydroxyanisole); soy protein and other serine protease inhibitors; paper mulberry extract; Glabridin (licorice extract); *Arctostaphylos patula* and *Arctostaphylos viscida* extracts; *Glycyrrhiza glabra* and its derivatives; *Chlorella vulgaris* extract; Magnesium-L-ascorbyl-2-phosphate (MAP); 4-Isopropylcatechol; Aleosin; N-acetyl-4-S-cysteaminylphenol and N-propionyl-4-S-cysteaminylphenol; N-acetyl glucosamine; and Tranexamic acid (trans -4-aminomethylcyclohexanecarboxylic acid); arbutin, bearberry extract, ascorbic acid and/or its derivatives, perilla extract (e.g., in U.S. Pat. No. 5,980,904 and Japanese Publications Nos. 07025742, 07187989, 10265322, 2001163759, and 2001181173, incorporated herein by reference), coconut fruit extract (Japanese Patent No. 2896815B2, incorporated by reference herein), coconut water, and calcium influx inhibitors, to name a few. Any of the tyrosine inhibitors disclosed in KR 2005095167; JP 2003252743; and JP 61260009, incorporated by reference herein, may be included, in some embodiments.

Other skin lighteners include extracts of *Butea frondosa, Naringi crenulata, Stenoloma chusana, Azadirachta indica, Glycyrrhiza glabra linn., Morinda citrifolia,* tomato glycolipid, ascorbyl glucoside, vitamin C, retinol and/or its derivatives, *rumex crispus* extract, milk proteins including hydrolyzed milk proteins, N,N,S-tris(carboxymethyl) cysteamine, oleanolic acids, placenta extract, saxifragia sarmentosa, juniperic acid, *ligusticum chiangxiong* hort., *asmunda japonica* thunb., *stellaria medica* (L.) cyr., *sedum sarmentosum* bunge, *ligusticum lucidum* Ait., *ilex purpurea* hassk, emblica, apigenin, ascorbyl palmitol, carruba *C. borealis* s, hesperitin, inabata *C. borealis,* isoliquirtigenin, kaempherol-7-neohesperidose, L-mimosine, luteolin, oil-soluble licorice extract P-T(40), oxa acid, phenyl isothiocyanate, cococin, silymarin, T4CA, teterahydro curcumin, unitrienol, ursolic-oleanolic acid, UVA/URSI, or any combinations thereof.

Any such additional depigmenting agents will typically be present, if at all, in amounts between about 0.001% and about 20% by weight, or 0.1 to 10% by weight based on the weight of the composition. In some embodiments of the invention, the compositions do not comprise additional depigmenting agents or will be essentially free of additional depigmenting agents, by which is meant that any additional tyrosinase inhibitors and/or melanosome-tranfer inhibitors will be present (if at all) in such low amounts as to not have a measurable or clinically observable effect on skin coloration.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbomers, and vegetable gums such as xanthan gum; gelling agents, such as ester-terminated polyester amides; structuring agents; metal chelating agents such as EDTA or salts thereof; pigments; colorants; and pH adjusters (citric acid, ethanolamine, sodium hydroxide, etc.). The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

In addition, the compositions contemplated by this disclosure can include one or more compatible cosmetically acceptable adjuvants commonly used and known by the skilled practitioner, such as colorants, pearls, chromalites, micas, pigments, dyes, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals. The topical compositions of the present disclosure may also include a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

A sunscreen may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. The composition is typically formulated as an emulsion, lotion, cream, ointment, serum or gel. The compositions can be formulated into liposomes which can comprise other additives or substances, and/or which can be modified to more specifically reach or remain at a site following administration.

In one embodiment, the topical composition will have a pH range from 1 to 8, with a pH in the range of from 2 to 7 being typical. In some embodiment, the composition will have a pH in the range of from 3.5 to 5.5. Suitable pH adjusters such as citric acid and triethanolamine may be added to bring the pH within the desired range.

Another embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

In certain embodiments, the cosmetic compositions described herein can be used to treat and/or prevent hyper-pigmentation of skin and/or that of the hair, for example, to lighten skin or hair. In some embodiments, a composition comprising an effective amount of a TDPA/niacinamide combination is topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, e.g., skin tanned due to UV exposure. Hyper-pigmented hair includes any shade of hair that is darker than desired.

Skin hyper-pigmentation may be caused by any number of factors, including, for example, genetics, UV or sun exposure, age, scarring, or discoloration due to skin injury, including lacerations, burns, sunburn, acne, or other dermatological conditions, and the like. For example, skin hyper-pigmented areas include melasmic patches. Melasma is a common skin disorder involving facial skin discoloration, one embodiment prevalent in pregnant women, where it is called chloasma faciei or chloasma. Melasmic (or chloasmic) patches may appear as dark brown, irregular patches on the face, on the upper cheeks, nose, lips, upper lip, and forehead. The patches often develop gradually over time and generally do not itch or otherwise hurt, but may negatively affect an individual's appearance. Skin hyper-pigmentation also refers to areas under the arm, e.g., that have become or are becoming darker than desired.

Skin hyper-pigmentation may or may not include areas under an individual's eyes that are darker than desired by the individual, commonly referred to as "under eye dark circles" or "dark circles." Dark circles are usually round, uniform areas of pigmentation beneath each eye, which may be caused by heredity, allergies, tiredness, or other causes. In one embodiment, the compositions are topically applied for the treatment of under eye dark circles. However, treatment of hyper-pigmentation, in some embodiments, excludes treating discoloration and/or bagginess in facial skin below the eyes because such pigmentation may entail an unrelated etiology to other hyperpigmentation conditions. Hyper-pigmented skin may also include skin in the axillary (i.e., underarm) region.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

The inventive compositions are capable of treating and/or preventing hyper-pigmented skin and can be referred to as "skin lighteners." When used for lightening hair, they can be referred to "hair lighteners." In one embodiment, the compositions of the present invention are usable to lighten hair in a non-bleaching manner; that is, by suppressing the formation and/or transportation of melanin out of follicular melanocytes, rather than by bleaching the hair itself. In one embodiment, the hair lightened by the instant invention includes facial hair (e.g., hair above the upper lip) and body hair (e.g., arms and legs), as opposed to scalp hair. In one embodiment, the hair lightener is applied to facial hair located on the upper lip.

The compositions are applied to the skin for a period of time sufficient to diminish the appearance of melanin in the skin. The compositions may be applied topically once, twice, or more daily. The treatment may be for a period of one week, two weeks, four weeks, eight weeks, or more. In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

In particular, a lightening composition comprising a lightening agent of nicotinamide or a precursor such as, for example, niacinamide ascorbate; a silicone compound of dimethyl polysiloxane; a sunscreen of 4-tertiary butyl-4'-methoxy dibenzyolmethane, 2-ethyl hexyl methoxy cynamate, or a mixture thereof; and a vehicle, is not contemplated as one of the lightening compositions described herein.

The present inventive compositions provide for products, especially skin care and cosmetic products that lighten skin in need thereof. Skin in need thereof includes, but is not limited to, dark complexions, hyperpigmented skin, age spots, liver spots, discolored or uneven skin, dark circles under the eyes for example, skin having melasma, cholasma, freckles, after-burn scars, post-injury hyperpigmented skin, skin, scalp, legs, face, and other areas where whitening or color reduction are desired, yellowed skin, stained nails, and the like. Also, the present compositions can be formulated to deliver a consistent level of an active ingredient, or blend of ingredients, so that a desired cosmetic effect is achieved.

One embodiment of the invention relates to methods of applying an effective amount of the lightening composition described herein, to lighten an affected area of the skin as used herein. The lightening composition is, in one embodiment, topical and applied once or twice daily, where the affected area of the skin that is in need of lightening includes, but is not limited to, the face, neck, hands, arms, legs, feet, thighs, hair, scalp, and overall body. The lightening composition may remain on the affected area in need of lightening or may be rinsed off or otherwise removed depending on the application. In order to maintain the desired lightening effect, the protocol should be continued for as long as the lightening effect is desired. Once the application of the lightening composition is discontinued, the desired lightening effect will also diminish.

In a related embodiment, the compositions of the invention are applied to human skin to reduce sebum production or improve the appearance of skin affected by cellulite, and/or reduce unwanted lipogenesis or increase lipolysis. In this embodiment, the compositions can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance therefof, including for example, daily treatment for at least four weeks, at least eight weeks, at least twelve weeks, or longer.

In some embodiments, the compounds of Formulas I(a) or I(b) will be used to treat signs of chronological and environmental aging, including reducing the severity of fine lines or wrinkles, treating thin skin, which includes thickening skin that has already thinned, and treating sagging skin. The compounds are often in combination with retinol in this embodiment.

The composition will typically be applied to the skin one, two, or three times daily for as long as is necessary to achieve desired results. The treatment regimen may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

In other embodiments, the compositions are topically applied to the skin to achieve an aesthetic improvement in skin. The aesthetic improvement of human skin may be an improvement of any attribute or characteristic of skin, including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness;
(r) reduction of pigment spots and/or mottled skin;
(s) improvement of optical properties of skin by light diffraction or reflection; and
(t) improvement in skin fairness.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

The following example illustrates a specific aspect of the instant description. The example should not be construed as limiting, as the example merely provides specific understanding and practice of the embodiments and its various aspects.

Example 1

Effect of 3,3'-Thiodipropanoic Acid and Nicotinamide on Melanin Levels

The effect of 3,3'-thiodipropanoic acid or Thiodipropionic acid (TDPA) and Nicotinamide on melanin levels was investigated using a MELANODERM™ (MEL-300-B, MatTek Corp., Ashland, Mass.) human skin model. MELANODERM™ is a viable reconstituted three-dimensional human skin equivalent containing melanocytes derived from African-American donors. Tissues were maintained in culture medium EPI-100-NMM-113 at 37° C. as recommended by the manufacturer.

TDPA was dissolved in water to a final concentration of 1.0% (w/v). Nicotinamide was dissolved in the culture media to a final concentration of 0.1% (w/v). 25 µl of the TDPA solution was applied topically to the MELANODERM™ tissue while 0.1% Nicotinamide containing culture medium was added on days 1, 2, 4, 7, 9, and 11. Control tissues were treated with water vehicle only. The tissue was treated with both active lightening agents at "saturated concentration," which is the highest concentration of treatment that is not toxic to the system.

On Day 14, tissues were collected and homogenized in a buffer containing 1% SDS, 50 mM EDTA, and 10 mM Tris, pH 6.8. To each homogenate, protease K (5 mg/ml) was added and incubated overnight at 45° C. Additional protease K was added and incubated for 4 hours at 45° C., followed by the addition of 0.5M sodium carbonate and 30% $H_2O_2$ and incubation at 80° C. for 30 minutes. The samples were cooled down to room temperature, and extracted with chloroform/methanol (2:1). After centrifugation at 10,000 g for 10 minutes, absorbance of the top phase was measured at 450 nm. Percent change in melanin levels in treated tissue was calculated relative to control. The average values of melanin levels of three tissues are shown in Table 1. TDPA and nicotinamide treatment alone showed significant reduction in melanin relative to control. But when the two were combined, they showed a further reduction in melanin which was statistically significantly greater than each one alone. Co-treatment of TDPA and nicotinamide resulted in a 26.3% decrease in melanin content, indicating that the magnitude of the melanin decrease was additive of the individually treated tissues.

Table 1 shows that co-treatment of TDPA and nicotinamide at saturated concentrations provides a full 100% additive effect on lightening. The reduction in melanin for the combination is more than about 60% than that using nicotinamide alone and more than about 160% than that using TDPA alone.

TABLE 1

PERCENT CHANGE IN MELANIN COMPARED TO WATER VEHICLE CONTROL IN 3D MELANODERM ™ TISSUE

| TREATMENT | % CHANGE IN MELANIN |
|---|---|
| TDPA 1% | −10%* |
| Nicotinamide 0.1% | −16%* |
| TDPA 1% + Nicotinamide 0.1% | −26.3%** |

*p < 0.05 vs vehicle control,
**p < 0.05 vs TDPA or Nicotinamide alone

Example 2

Effect of 3,3'-Thiodipropanoic Acid and Kojic Acid on Melanin Levels

The effects of 3,3'-thiodipropanoic acid and Kojic acid on melanin levels were determined by performing assays using B16 melanoma cells. These cells are known to constitutively produce melanin and are a commonly utilized and accepted model system for monitoring the inhibition of melanin synthesis.

The B16 mouse melanoma cells were seeded (ATCC, cat. #: CRL-6475) into 96-well tissue culture-treated plates (BD Falcon) and treated with test actives or controls in DMEM without phenol red (Mediatech; cat. #: 17-205-CV). The cells were examined for their ability to modulate pigment formation. Cells were exposed to diluted test actives or control, where kojic acid had a final concentration of 0.01%, TDPA had a final concentration of 0.1%, and 2 microliters water vehicle control per 200 microliters final volume was used, over a period for 7 days. Tests were performed in 6 replicates each. Following the treatment period, the level of pigment produced or melanin synthesized was quantified by reading the absorbance at 540 nm using a standard microplate reader (Tecan Group Ltd.).

After quantifying the amount of melanin, cell viability was determined using the MTT conversion method. The MTT conversion method measures the reduction of the MTT dye from a yellow colored, water-soluble, tetrazolium salt to a bluish-purple colored insoluble formazan precipitate by NAD(P)H-dependent microsomal dehydrogenase enzymes, which only function in viable cells. The intensity of the blue color is indicative of cell viability. After quantifying the amount of melanin pigment produced, the cells were exposed to MTT dye solution (1 mg/ml) for two to three hours. Formazan material was solubilized with reagent alcohol (95% ethanol: 5% isopropanol) and shaken on an orbital shaker for 15-30 minutes. MTT dye uptake and conversion by viable cells were determined by measuring the extracted formazan at 570 nm using a microplate reader. Total pigmentation was calculated, normalized to cell viability values and expressed as the average percent change in melanin level relative to control of sextuplicates performed.

Table 2 shows the effect of co-treatment with kojic acid, a known whitening agent, and TDPA on melanin levels using a B16 melanoma cell assay. Although individually, kojic acid, a positive control for whitening, and TDPA treated cells showed some decrease in percent change in pigmentation, there was no significant difference between kojic acid alone and co-treatment of kojic acid and TDPA. If the combination were to have had additive effects, then the expected percent decrease would have been 75% and not 46.9%. This suggests that the combination of simply any depigmenting agents does not necessarily result in an additive depigmenting effect.

TABLE 2

PERCENT CHANGE IN MELANIN COMPARED TO WATER VEHICLE CONTROL IN B16 CELL ASSAY

| TREATMENT | % CHANGE IN MELANIN |
|---|---|
| TDPA 0.1% | −27.4%* |
| Kojic Acid 0.01% | −47.6%* |
| TDPA 0.1% + Kojic Acid 0.01% | −46.9%*# |

*p < 0.05 vs vehicle control,
p < 0.05 vs TDPA or but not to Kojic Acid

Example 3

Effect of 3,3'-Thiodipropanoic Acid and STI on Melanin Levels

The effect of TDPA and Soybean Trypsin Inhibitor (STI) on melanin levels was investigated using the MELANODERM™ human skin model according to the methods described in Example 1.

Table 3 shows the effect of co-treatment with STI, a known melanosome transfer inhibitor, and TDPA on melanin levels. There was little difference between the percent change in melanin decrease for the STI and TDPA treated cells individually, compared with the percent change in melanin decrease for the cells co-treated with STI and TDPA. If the combination were to have had additive effects, then the expected percent decrease would have been 18% and not 11.9%. This suggests that the combination of a tyrosinase inhibitor and melanosome transfer inhibitor would not have been expected to provide a fully additive depigmenting effect.

PERCENT CHANGE IN MELANIN COMPARED TO WATER VEHICLE CONTROL IN 3D MELANODERM ™ TISSUE

| TREATMENT | % CHANGE IN MELANIN |
|---|---|
| TDPA 1% | −9.1% |
| STI 0.1% | −8.9% |
| TDPA 1% + STI 0.1% | −11.9% |

Example 4

This Example provides an exemplary formulation for a skin lightening cosmetic with additional anti-aging benefits. All ingredient amounts are designated as (w/w) percentages of the entire exemplary cosmetic composition.

| Ingredient | Amount |
|---|---|
| Demineralized water | q.s. |
| Carbopol 934 | 0-0.01-1% |
| Acrylates/C10-30 Alkyl Acrylate Crosspolymer | 0-0.01-1% |
| Xanthan gum | 0-0.001-1% |
| Disodium EDTA | 0-0.001-1% |
| Methylparaben | 0-0.001-1% |
| Ethanol | 0-0.1-10% |
| Phenoxyethanol | 0-0.001-1% |

-continued

| Ingredient | Amount |
|---|---|
| Butylene glycol | 0-0.1-5% |
| Pentylene glycol | 0-0.1-5% |
| Ethoxydiglycol | 0-0.01-2% |
| Isododecane (IDD) | 0-0.1-3% |
| Dilauryl Thiodipropionate | 0-0.1-1% |
| Tetrahexadecyl Ascorbate | 0-0.1-1% |
| Ascorbyl Glucoside | 0-0.1-2% |
| Glycyrrhizinate-Dipotassium | 0-0.1-1% |
| Silica shells | 0-0.1-1% |
| NaOH (50% solution) | 0-0.01-3% |
| Silicone Fluid SF-96-5 | 0-0.1-2% |
| PEG-40 Stearate | 0-0.1-1% |
| Steareth-2 | 0-0.1-1% |
| *Saxifraga sarmentosa*/Grape extract | 0-0.1-1% |
| *Sacchromyces*/Zinc Ferment | 0-0.1-1% |
| Yeast Extract | 0-0.1-1% |
| Soybean extract | 0-0.1-1% |
| Carrot root extract | 0-0.1-1% |
| Phytol | 0-0.01-1% |
| Dimethicone/Dimeth. Crosspolymer | 0-0.01-2% |
| 3,3'-thiodipropionic acid (TDPA) | 0.1-2% |
| Niacinamide | 0.01-1% |
| Silicone cross-polymer | 0.01-10% |

Example 5

This Example provides an exemplary formulation for a deodorant with skin lightening benefits. All ingredient amounts are designated as (w/w) percentages of the entire exemplary cosmetic composition.

| Ingredient | Amount |
|---|---|
| Demineralized water | q.s. |
| POP (15M) stearyl ether | 1-3% |
| Isopropyl Palmitate | 1-3% |
| Steareth-2 | 1-4% |
| Aluminum Chlorohydrate | 1-25% |
| TDPA | 0.1-2% |
| Niacinamide | 0.01-1% |

The Aluminum Chlorohydrate may be replaced by Aluminum zirconium trichlorohydrate in an amount up to 20% by weight. The composition is in the form of a solid stick and is applied to the underarm daily to reduce the axillary pigmentation.

The contents of all patents, patent applications, published articles, abstracts, books, reference manuals and abstracts, as cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

What is claimed is:

1. A topical composition for reducing pigmentation in human skin, comprising: (i) 3,3'-thiodipropionic acid, or a salt or ester thereof, and (ii) nicotinamide, or salt thereof, or melanosome-transfer inhibiting derivative thereof, and (iii) a cosmetically or dermatologically acceptable vehicle, wherein the 3,3'-thiodipropionic acid, or salt or ester thereof, is present in an effective amount ranging from about 0.1% (w/w) to about 2.5% (w/w) based on the total weight of the composition and the nicotinamide, or salt thereof, or melanosome-transfer inhibiting derivative thereof, is present in an effective amount ranging from about 0.01% (w/w) to about 1% (w/w) based on the total weight of the composition, and wherein the effective amount of 3,3'-thiodipropionic acid, or salt or ester thereof, and effective amount of nicotinamide, or salt thereof, or melanosome-transfer inhibiting derivative thereof together provide at least 25% greater relative reduction in melanin synthesis than either component alone.

2. The composition according to claim 1, wherein the composition comprises an ester of 3,3'-thiodipropionic acid having the structure of the structure of formula I:

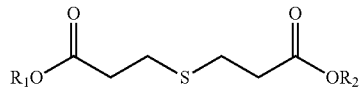

wherein $R_1$ and $R_2$ are independently selected from hydrogen, a group L, or a group $R^a$, where $R^a$ is independently at each occurrence an aliphatic $C_{1-20}$ hydrocarbon radical; an aromatic $C_{6-12}$ hydrocarbon radical; a $C_{6-20}$ alkyl-aryl hydrocarbon radical; a $C_{6-20}$ aryl-alkyl hydrocarbon radical; or a heteroaromatic radical, each of the foregoing being optionally substituted with a group R or with 1-6 heteroatoms selected from nitrogen, oxygen, sulfur, or halogen;

wherein L is a group of the form $—X_1—(CR^*_2)_n—X_2—(CR^*_2)_m—X_3—$; wherein $X_1$, $X_2$, and $X_3$ are independently at each occurrence a bond, $—O—$, $—NR^N—$, $—S—$, $—(OCH_2CH_2)_p—$, $—CH_2CH_2O)_q—$, or a group $R^*$, wherein "p" and "q" are independently an integer from 1 to 10, and "n" and "m" are independently an integer from 0 to 10;

R is independently at each occurrence selected from hydrogen, $—F$; $—Cl$; $—Br$; $—I$; $—OH$, $—OR^*$; $—NH_2$; $—NHR^*$; $—N(R^*)_2$; $—N(R^*)_3$; $—N(R^*)—OH$; $—N(\rightarrow O)(R^*)_2$; $—O—N(R^*)_2$; $—N(R^*)—O—R^*$; $—N(R^*)—N(R^*)_2$; $—C=N—R^*$; $—N=C(R^*)_2$; $—C=N—N(R^*)_2$; $—C(=NR^*)—N(R^*)_2$; $—SH$; $—SR^*$; $—CN$; $—NC$; $—(C=O)—R^*$; $—CHO$; $—CO_2H$; $—CO_2^-$; $—CO_2R^*$; $—(C=O)—S—R^*$; $—O—(C=O)—H$; $—O—(C=O)—R^*$; $—S—(C=O)—R^*$; $—(C=O)—NH_2$; $—(C=O)—N(R^*)_2$; $—(C=O)—NHNH_2$; $—O—(C=O)—NHNH_2$; $—(C=S)—NH_2$; $—(C=S)—N(R^*)_2$; $—N(R^*)—CHO$; $—N(R^*)—(C=O)—R^*$; $—(C=NR)—O—R^*$; $—O—(C=NR^*)—R^*$, $—SCN$; $—NCS$; $—NSO$; $—SSR^*$; $—N(R^*)—C(=O)—N(R^*)_2$; $—N(R^*)—C(=S)—N(R^*)_2$; $—SO_2—R^*$; $—O—S(=O)_2—R^*$; $—S(=O)_2—OR^*$; $—N(R^*)—SO_2—R^*$; $—SO_2—N(R^*)_2$; $—O—SO_3^-$; $—O—S(=O)_2—OR^*$; $—O—S(=O)—OR^*$; $—O—S(=O)—R^*$; $—S(=O)—OR^*$; $—S(=O)—R^*$; $—NO$; $—NO_2$; $—NO_3$; $—O—NO$; $—O—NO_2$; $—N_3$; $—N_2—R^*$; $—N(C_2H_4)$; $—Si(R^*)_3$; $—CF_3$; $—O—CF_3$; $—PR^*_2$; $—O—P(=O)(OR^*)_2$; $—P(=O)(OR^*)_2$; perfluoroalkyl; an aliphatic $C_1$-$C_{12}$ hydrocarbon radical; a $C_6$-$C_{12}$ aromatic hydrocarbon radical; a $C_5$-$C_{12}$ heteroaryl radical;

$R^N$ and R* are selected independently from hydrogen or a saturated, partially saturated, or aromatic $C_1$-$C_{20}$ hydrocarbon radical, optionally substituted with a group R or with 1-6 heteroatoms selected from nitrogen, oxygen, sulfur, or halogen;

with the proviso that at least one of $R_1$ and $R_2$ is a group L or R*; and salts thereof.

3. The composition according to claim 2, wherein $R_1$ and $R_2$ are each independently selected from $C_{1-20}$ aliphatic hydrocarbon radicals.

4. The composition according to claim 3, wherein the 3,3'-thiodipropionic acid, or salt or ester thereof comprises di-lauryl-3,3'-thiodipropionate.

5. The composition according to claim 1, wherein said melanosome-transfer inhibiting derivative of nicotinamide has the structure of the structure of formula II:

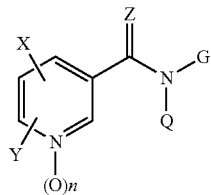

wherein "n" is an integer 0 or 1;

Z is selected from the group consisting of O, S, NH, and $NR^N$;

G and Q are independently selected from the group consisting of hydrogen, $R^N$, —COR, —CO$_2$R, —C(=O)NHR, —C(=O)NR$_2$, —PO$_3$R, —S(O)$_m$R, —NHR, —N=CHR, —NR(C=O)R; and —NRCO$_2$R;

where "m" is 0, 1, or 2; and wherein G and Q may together form a 3-6 membered heterocyclic ring; and where Z and G may together form a 5 or 6-member heterocylic ring;

X and Y are independently selected from groups R; and where X and Y may together to form 4-6 membered ring;

R is independently at each occurrence selected from hydrogen, —F; —Cl; —Br; —I; —OH, —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{12}$ hydrocarbon radical; a $C_6$-$C_{12}$ aromatic hydrocarbon radical; and a $C_3$-$C_{12}$ heteroaryl radical;

$R^N$ and R* are selected independently from hydrogen or a saturated, partially saturated, or aromatic $C_1$-$C_{20}$ hydrocarbon radical, optionally substituted with a group R or with 1-6 heteroatoms selected from nitrogen, oxygen, sulfur, or halogen;

or a salt thereof.

6. The composition according to claim 1, wherein the 3,3'-thiodipropionic acid, or a salt or ester thereof, and the nicotinamide, or salt or derivative thereof, are present in a ratio ranging from about 5:1 (w/w) to about 1:5 (w/w) based on the total weight of the composition.

7. The composition according to claim 1, wherein the 3,3'-thiodipropionic acid, or a salt or ester thereof and the nicotinamide, or salt or derivative thereof, are present in a ratio of about 10:1 (w/w) based on the total weight of the composition.

8. The topical composition according to claim 1, wherein the cosmetically or dermatologically acceptable vehicle comprises a water-in-oil, oil-in-water, water-in-silicone, silicone-in-water, polyol-in-silicone, or silicone-in-polyol emulsion, and further comprises from about 0.001% to about 20% by weight of an emulsifier.

9. A method of reducing pigmentation in human skin, comprising topically applying to an area of skin the composition according to claim 1.

10. The method according to claim 9, wherein said composition is applied to the skin at least once daily for a period of one week or more.

11. The method according to claim 9, wherein said composition is applied to the skin at least once daily for a period of one four weeks or more.

12. The method according to claim 3, wherein the skin suffers from one or more of dark complexion, pigmented skin discoloration, pigmented birthmarks, hyperpigmentation, post-inflammatory hyperpigmentation, post-injury hyperpigmentation, freckles, age spots, liver spots, sun damage, tans, pigmented acne marks, scars, melasma, cholasma, after-burn scars, nail stains, yellowing of skin, or dark circles under eye.

* * * * *